(12) United States Patent
Fumex et al.

(10) Patent No.: US 12,108,943 B2
(45) Date of Patent: Oct. 8, 2024

(54) COUPLER AND SURGICAL DEVICE WITH COLLAR FOR COVERING A STERILE FLEXIBLE WRAPPER

(71) Applicant: Varian Medical Systems, Inc., Palo Alto, CA (US)

(72) Inventors: Laurent Fumex, Madison, CT (US); Thierry Masseglia, La Garde (FR)

(73) Assignee: Varian Medical Systems, Inc., Palo Alto, CA (US)

( * ) Notice: Subject to any disclaimer, the term of this patent is extended or adjusted under 35 U.S.C. 154(b) by 871 days.

(21) Appl. No.: 17/180,060

(22) Filed: Feb. 19, 2021

(65) Prior Publication Data

US 2021/0219965 A1    Jul. 22, 2021

(30) Foreign Application Priority Data

Feb. 24, 2020   (FR) ...................................... 2001807

(51) Int. Cl.
*A61B 10/02*   (2006.01)
*A61B 17/34*   (2006.01)
(Continued)

(52) U.S. Cl.
CPC ........ *A61B 10/025* (2013.01); *A61B 17/3472* (2013.01); *A61B 46/10* (2016.02);
(Continued)

(58) Field of Classification Search
None
See application file for complete search history.

(56) References Cited

U.S. PATENT DOCUMENTS 6,309,358 B1    10/2001  Okubo
2008/0045860 A1  2/2008  Miller et al.
(Continued)

FOREIGN PATENT DOCUMENTS

WO    2017/046531    3/2017

OTHER PUBLICATIONS

Search Report dated Oct. 9, 2020.

*Primary Examiner* — Benjamin S Melhus
*Assistant Examiner* — Samuel C Kim
(74) *Attorney, Agent, or Firm* — Duane Morris LLP (57) ABSTRACT

A coupler (2) for the sterile coupling of a percutaneous surgical instrument to a rotational-driving tool (3), extending along a coupling axis (A). The coupler (2) has a distal portion (27) configured to be connected removably to a percutaneous surgical instrument, a proximal portion (28) configured to be connected removably to a driving tool (3), a central portion (29) arranged between the distal (27) and proximal (28) portions. The central portion has a bearing collar (240) extending transversely to the coupling axis (A) and configured to axially deform a distal end of a flexible wrapper (1) surrounding the driving tool (3) when the proximal portion (28) is connected to this driving tool (3). The central portion also has a retaining collar (243) extending along the coupling axis (A) at least partially covering the proximal portion (28) to keep the distal end of the sterile flexible wrapper (1) between the retaining collar (243) and the housing (36) of a driving tool (3) when the proximal portion (28) is connected to the driving tool (3).

17 Claims, 8 Drawing Sheets

(51) Int. Cl.
*A61B 46/10* (2016.01)
*A61B 17/00* (2006.01)
(52) U.S. Cl.
CPC .............. *A61B 2010/0258* (2013.01); *A61B 2017/00477* (2013.01)

(56) References Cited

U.S. PATENT DOCUMENTS

| | | | |
|---|---|---|---|
| 2009/0240214 A1* | 9/2009 | Conway | A61M 25/002 |
| | | | 206/572 |
| 2015/0129456 A1* | 5/2015 | Miller | A61B 46/10 |
| | | | 206/571 |
| 2017/0027658 A1 | 2/2017 | Black et al. | |
| 2017/0325791 A1 | 11/2017 | Fumex et al. | |
| 2022/0338947 A1* | 10/2022 | Cancilla | A61B 50/30 |

* cited by examiner

Fig. 11

COUPLER AND SURGICAL DEVICE WITH COLLAR FOR COVERING A STERILE FLEXIBLE WRAPPER

RELATED APPLICATION

This application claims the benefit of priority from French Patent Application No. 20 01807, filed on Feb. 24, 2020, the entirety of which is incorporated by reference.

FIELD OF THE INVENTION

The invention relates to the overall field of percutaneous surgical instrumentation. It relates more specifically to percutaneous surgical instruments intended to pass through the epidermis and the soft parts of the body in order, for example, to take samples of bone marrow and bone tissue for biopsy purposes.

DESCRIPTION OF THE RELATED ART

In the field of percutaneous surgery and, more particularly, that of percutaneous bone-marrow biopsy and bone biopsy, it is known practice to employ various instruments that are able both to penetrate the skin and then the soft tissues and then the cortex of the bone concerned and to take samples of organic substances (bone marrow, bone samples) contained in the bone or in bone cavity.

These instruments are generally known by the name of bone marrow biopsy or bone biopsy needles or trocars, and can generally comprise an access trocar or needle, that may be combined with a biopsy cannula. Being more or less perforating in nature, the access trocars or needles allow the practitioner to pass through the soft tissues then bore into the bone concerned so as to reach what is known as the sampling zone.

These trocars generally comprise a hollow external tube, the end of which is more or less cutting, inside which there slides a rod referred to as a punch or a stylet, the end of which is sharpened in order to perforate the bone cortex. The bone or bone marrow tissue sample may be taken by this rod itself or by the hollow external tube. In that case, the rod is temporarily withdrawn from the tube and the latter is pushed or screwed further in so as to capture the sample. In another configuration, a biopsy cannula of varying shape is introduced into the tube in place of the rod and so as to take the bone marrow or bone sample.

Such instruments are generally operated manually by means of a handle secured, permanently or otherwise, to the proximal end (the end that does not come into contact with the bone) of the perforating rod, and that the practitioner turns in order to bore into the bone. In practice, the practitioner brings the end of the external tube of the trocar into contact with the bone and then turns the handle in order to cause the end of the rod to penetrate the bone.

Thus, international publication published under the reference WO2006/061514 describes a trocar intended for bone biopsy comprising an external tube of which the distal end is divided into two segments with helical cutting edge, and in which a sharpened rod slides. This type of instrument is intended to be operated manually by means of a handle.

Manual use of such a trocar, by means of a handle operated directed by the practitioner, is a conventional method of operation that allows the practitioner fine control over the action of perforating the bone. However, in certain circumstances, particularly when the hardness of the bone requires greater vigor in order to be able to cause the needle to penetrate through the wall of the bone, it is then sometimes more comfortable, both for the patient and for the practitioner, to have the use of a driving tool, of motorized type, in order to cause the rod to penetrate into the bone without applying excessive force.

OBJECTS AND SUMMARY

There is therefore a great advantage to the practitioner in being able to have a trocar of which the perforating rod can be actuated indifferently either by means of a simple handle or by means of a driving tool.

Such a possibility advantageously allows the practitioner to begin an operating procedure manually and then, if the hardness of the bone so dictates, to complete the perforation using an automatic rotational-drive, and to do so without the need to change the perforating rod and therefore without the risk of losing the point of entry into the bone.

To do that, an interface device capable via one of its ends of taking the place of the handle used by the practitioner can be used to operate the trocar manually; by being mounted for example at the end of the latter in exactly the same way as the handle, and at its other end bearing an interface element to which the end piece of a driving tool can be removably attached.

The device of the present invention relates to a coupling element that allows the trocar to be rotationally driven by means of a tool.

The objective of such a device is, amongst other functions, that of being able to provide relatively precise axial positioning of the driving tool with respect to the trocar, without which the penetration precision of the trocar could be adversely affected.

In addition, the interface device is intended to provide the connection between the end of a trocar, which is a sterile and generally single-use object, with a tool of the drill type, which is an object which is naturally reusable and generally nonsterile. It is therefore preferable for the interface device to be able to be associated in a simple way with means that allow the driving tool to be mounted on the end of the trocar and that allow said trocar to be rotationally driven while avoiding any contact between the trocar and the driving tool, which contact is liable to cause the one to be contaminated by the other.

U.S. Pat. No. 6,716,215 B1 describes a means that offers a solution for connecting a sterile drill bit to a non-sterile drill through a sterile bag. The sterile bag, to which a ring is fixed, is intended to receive a drill that it is able to wrap so that it can be used in a sterile environment.

In the region of connection of the drill to the drill bit, sealing is achieved by means of a toric seal, housed in the ring, which creates a seal onto the body of the drill bit. Sealing is achieved by the compressing of the seal.

This solution does however have the disadvantage that the bag may find itself rotationally driven as a result of the friction of the seal against the drill bit and that it may therefore, by turning, block the rotation of the drill.

U.S. Pat. No. 7,850,620 B2 describes a system allowing a motorized device, which is nonsterile and housed in a sterile bag, to be connected to a sterile biopsy instrument by means of a coupler secured to the bag. The assembled coupler comprises a ring blocked in translation but free to rotate and to which the bag is welded. This solution does not allow a complete seal to be created because the ring may allow impurities to pass because of its operating clearance.

Moreover, a device as described in U.S. Pat. No. 7,850, 620 B2 does not exclude the risk that, given the structure of the assembled coupler, the bag might be rotationally driven under the effect of friction and might thus block the rotation of the drill by tightening around a rotating element.

The device described in U.S. Pat. No. 7,850,620 B2 does not make it possible to ensure good concentricity of the assembly during use by the practitioner because of the cumulative effect of the functional clearances between the various assemblies. The functional clearance of the instrument mounted in the assembled coupler, added to the functional clearances of the various components of the assembled coupler, added to the functional clearance of the assembled coupler mounted on the drive shaft of the driving tool mean that the end of the instrument is ultimately unstable with respect to the driving tool, something which is troublesome for the practitioner and disadvantageous for the precision of the surgical operation.

Finally, the number of components that make up this device and the relative arrangement thereof, lead to high costs of manufacture.

Patent application EP 1 771 034 A1 describes a system that allows a non-sterile motorized device of the drill type, housed in a sterile bag, to be coupled to a sterile biopsy instrument by means of a coupler. The bag comprises a ring the shape of which is able to conform to the shape of the tip of the drill. A key-shaped lug on the tip of the drill and a boss on the ring allow the ring to be secured to the drill while blocking any rotation of the bag around the drill. Thus, when the drill fitted with its coupler is placed inside the bag, the ring and the bag are blocked in terms of rotation by the key-shaped lug, this being in spite of the friction between the seal of the bag and the body of the coupler. This solution allows both sealing of the bag and rotational blocking thereof.

However, because the motorized device is reusable, it requires meticulous cleaning which is difficult to achieve with the presence of the key-shaped lugs or of any other protuberance having fairly sharp edges. In addition, the coupling end piece of the drill has machinings that leave regions that are difficult to clean, and because the body of the drill does not cover the coupling end piece, there is nothing to stop impurities from being ejected under the effect of the centrifugal force generated by the rotary movement of the drill combined with the aging of the bag seal under the effect of friction and of the heat thus released. The orientation of the fold of the seal toward the sterile surgical instrument may make it easier for impurities to be thrown out toward the patient during the intervention under the combined effect of the centrifugal force, the aging of the seal and of the air trapped in the bag and exiting via the seal. This approach requires good concentricity of the opening made in the bag with respect to the ring in order to avoid ovalization of the fold around the body of the coupler. Such precision is difficult to obtain because the bag is made from flexible and therefore highly deformable, materials.

There is therefore still a need for a device for coupling a driving tool to a percutaneous surgical instrument that does not have the abovementioned disadvantages.

It is an object of the present invention to provide a coupling device of simple design and low cost but that also makes it possible to ensure a good seal between the sterile and non-sterile elements that are coupled together.

Another object of the present invention is to guarantee good concentricity and good alignment between the percutaneous surgical instrument and the driving tool so as to obtain precise positioning of the instrument.

A further object of the present invention is to limit the operating clearances induced by the coupling device in order to guarantee precise positioning of the surgical instrument and thus make it easier to use.

To do that, the invention relates to a coupler for the sterile coupling of a percutaneous surgical instrument to a rotational-driving tool, extending along a coupling axis, said coupler comprising:
  a distal portion configured to be connected removably to a percutaneous surgical instrument,
  a proximal portion configured to be connected removably to a driving tool,
  a central portion arranged between the distal and proximal portions, the central portion comprising:
    a bearing collar extending transversely to the coupling axis and configured to axially deform a distal end of a flexible wrapper surrounding the driving tool when the proximal portion is connected to this driving tool,
    a retaining collar extending along the coupling axis at least partially covering the proximal portion so as to be able to keep the distal end of the sterile flexible wrapper between the retaining collar and the housing of a driving tool when the proximal portion is connected to the driving tool, wherein the coupler forms a unit accessory in which the distal, proximal and central portions are secured to one another.

The arrangement of the bearing and retaining collars makes it possible to form a significant obstacle to the propagation of impurities between the distal portion of the coupler that is to be protected from the impurities and the proximal portion at which the impurities may be generated, notably from a connection end piece of the driving tool.

This obstacle to the propagation of impurities is both transverse with respect to the axis of rotation of the coupler, by means of the bearing collar, and longitudinal to this axis of rotation, by means of the retaining collar.

In addition, the deformation of the end of the flexible wrapper by the bearing collar allows the end of the flexible wrapper to be used as an additional obstacle to the propagation of impurities at the proximal end of the coupler. This increases still further the difficulty that impurities have in leaving the end of the driving tool and reaching the distal portion of the coupler which portion is intended to be arranged in a sterile environment.

According to one embodiment of the coupler, the distal, proximal and central portions are fixed relative to one another.

According to one embodiment of the coupler, the retaining collar extends about the coupling axis in such a way as to form a protective bell configured to cover a connection end of a driving tool.

According to one embodiment of the coupler, the central portion comprises a connecting body arranged between the distal and proximal portions, the bearing collar extending from the connecting body and forming, with the retaining collar the overall shape of a U.

According to one embodiment of the coupler, the retaining collar extends from one end of the bearing collar to form an annular space around the central portion. The bearing and retaining collars thus form a wall bent over toward the proximal portion and therefore toward the driving tool when the latter is connected to the coupler. This bent-over wall thus makes it possible to prevent any impurities that might come from the driving tool from being thrown toward the distal portion at which there is the sterile environment.

The bearing and retaining collars thus form a protective skirt at least partially covering the proximal portion and therefore the end of the driving tool.

According to one embodiment of the coupler, the central portion further comprises a protective collar extending along the coupling axis between the retaining collar and the proximal portion. An additional barrier is thus formed across the passage of potential impurities that might come from the driving tool. This makes it possible to increase the chance of halting the spread of these impurities in order to limit still further the risks of contamination of the sterile environment. The protective collar may also extend in such a way as to at least partially cover the proximal portion. In this way, the obstacle formed by the protective collar is all the more significant and forms an additional turn in the path adopted by potential impurities.

According to one embodiment of the coupler, the proximal portion is a male connection configured to connect to a female connection end piece of a driving tool.

The invention also relates to a sterile surgical device for rotationally driving a percutaneous surgical instrument, comprising:
 a coupler as described above,
 a flexible wrapper forming:
  a receiving cavity to receive a driving tool,
  a first opening configured to allow the driving tool to be inserted inside the receiving cavity,
  an end portion configured to receive a connection end of the driving tool, the end portion forming a second opening into the receiving cavity and configured to allow partial insertion of the coupler inside the receiving cavity through the second opening,
  an annular sealing portion, configured to be received in contact with the annular surface of the housing of the driving tool when the connection end of the driving tool is inserted into the end portion of the wrapper,
 the retaining collar of the coupler being configured to at least partially cover the annular portion of the wrapper when the connection end of the driving tool is inserted into the end portion of the wrapper with the proximal portion of the coupler connected to the connection end piece.

According to one embodiment of the surgical device, the latter further comprises:
 a driving tool comprising:
  a housing and a rotational-drive member arranged inside the housing, the housing defining an annular surface for receiving a flexible wrapper at a connection end of the driving tool,
  a connection end piece arranged at the connection end and configured to be connected removably to the proximal portion of the coupler, the connection end piece being secured to the drive member in such a way as to transmit a rotational movement of the drive member to the coupler when the proximal portion is connected to the connection end piece.

According to one embodiment of the surgical device, the wrapper has no rigid component for connection to the driving tool or to the coupler, when the driving tool, the coupler and the wrapper are in the disconnected state.

The cost of manufacturing the wrapper is thus greatly reduced in comparison with a wrapper to which a ring is fixed, as described for example in U.S. Pat. No. 7,850,620 B2. In addition, the securing of the wrapper to the driving tool becomes easier because the driving tool can be positioned in the end portion of the wrapper under the effect of gravity without the need to align fixing shapes or mechanisms.

According to one embodiment of the surgical device, the annular portion of the wrapper and the annular surface of the housing of the driving tool have complementing shapes. Thus, the annular portion of the wrapper fits over the annular surface of the housing of the driving tool in order to limit the spread of impurities from the inside to the outside of the wrapper.

According to one embodiment of the surgical device, the annular portion of the wrapper has a cross section at least partially smaller than the cross section at the annular surface of the housing of the driving tool so as to deform the wrapper when the driving tool is inserted into the end portion with the annular portion and the annular surface in contact with one another.

According to one embodiment of the surgical device, the annular portion and the annular surface have a conically tapering cross section respectively tapering toward the second opening and the connection end piece. This conically tapering shape allows the annular surface of the driving tool to fit the annular portion of the wrapper as closely as possible.

According to one embodiment of the surgical device, the annular portion of the wrapper is contiguous with the end portion.

According to one embodiment of the surgical device, the wrapper is formed by at least two sheets joined together at their end edges to form the receiving cavity, a return substantially transverse to the sheets being formed along the end edges.

According to one embodiment of the surgical device, said at least two sheets are fixed together by welding.

According to one embodiment of the surgical device, the retaining collar extends in such a way as to cover at least one third of the length of the annular portion along the coupling axis when the driving tool is connected to the coupler. This allows a good compromise between the amount of surface covered by the retaining collar and the ease of mounting of the coupler. Specifically, the longer the retaining collar, the greater the reduction in the visibility that allows the proximal part of the coupler to be oriented and inserted into the driving tool.

According to one embodiment of the surgical device, the retaining collar comprises a distal end arranged at the level of the central portion of the coupler, and a free proximal end, the retaining collar and the annular surface of the driving tool being dimensioned to form a clearance less than or equal to 3 mm, preferably less than or equal to 2 mm, between the proximal end of the retaining collar and the annular surface of the driving tool when the driving tool is connected to the coupler. The space that separates the connection end of the driving tool from the retaining collar is thus very small. This prevents the spread of impurities still further because this space is also occupied on the one hand by the proximal end of the wrapper deformed by the bearing collar and, on the other hand, by the end edges of the wrapper pressing against the internal face of the retaining collar.

DETAILED DESCRIPTION

The concept of the invention is described more fully hereinafter with reference to the attached drawings, which show embodiments of the inventive concept. For the sake of clarity, the size and relative sizes of the elements may have been exaggerated in the drawings. Similar reference numbers refer to similar elements across all the drawings. However, this concept of the invention can be implemented in numerous different forms and should not be interpreted as being limited to the embodiments set forth here. Rather, these embodiments are proposed in order to make this description complete, and communicate the extent of the inventive concept to those skilled in the art.

Throughout the specification, a reference to "an embodiment" means that a function, a structure, or a particular feature described in relation to an embodiment is included in at least one embodiment of the present invention. Thus, where the expression "in one embodiment" appears at various points throughout the specification, this does not necessarily refer to the one same embodiment. Furthermore, the functionalities, structures or particular features may be combined in absolutely any appropriate way in one or more embodiments. In addition, the term "comprising" does not exclude there being other elements or steps.

Figure 1:
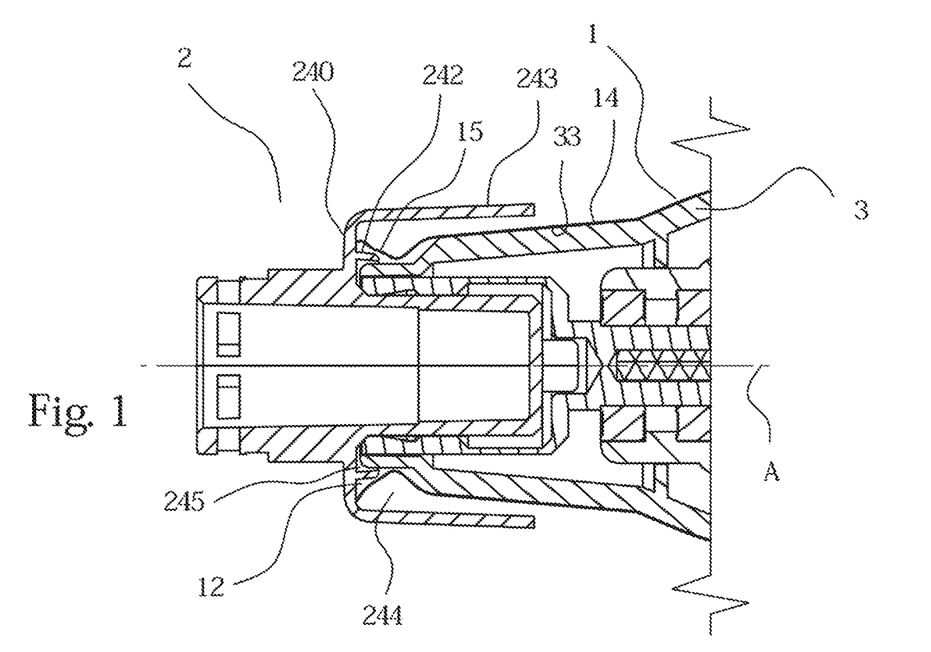
FIG. 1 depicts a view in cross section of a coupler connected to a connection end of a driving tool, a flexible wrapper being positioned around the driving tool between a retaining collar of the coupler and the connection end of the driving tool.
Figure 2:
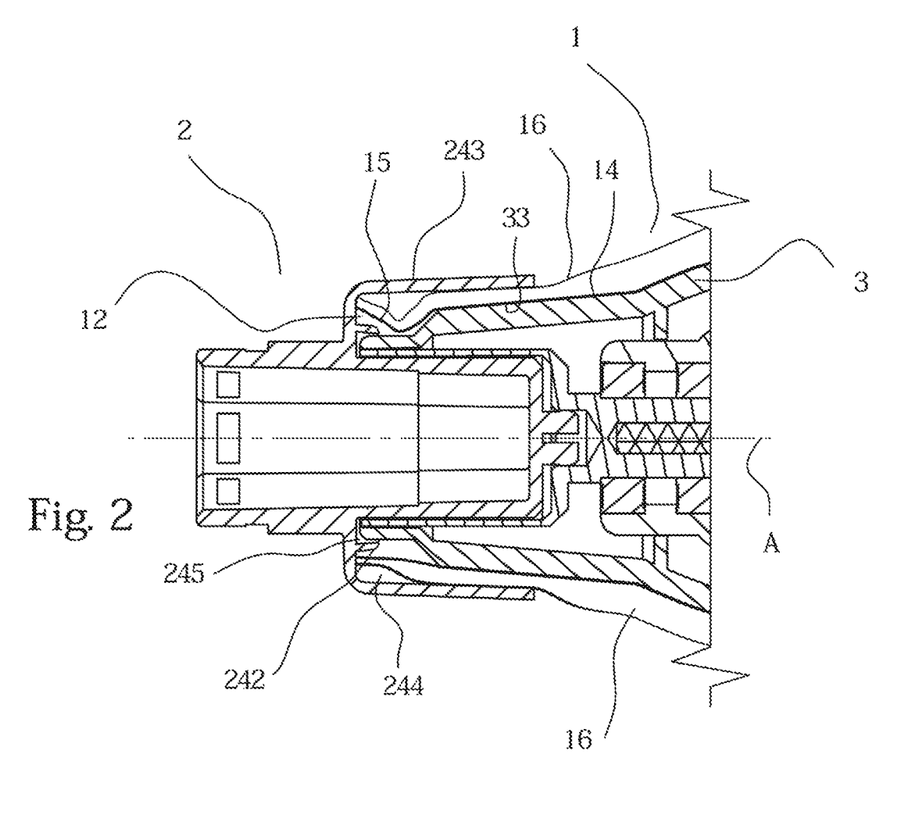
FIG. 2 depicts a view in cross section of the coupler connected to the driving tool as visible in FIG. 1, in a different angular position of the plane of section, thus showing a transverse return of the wrapper.
Figure 3:
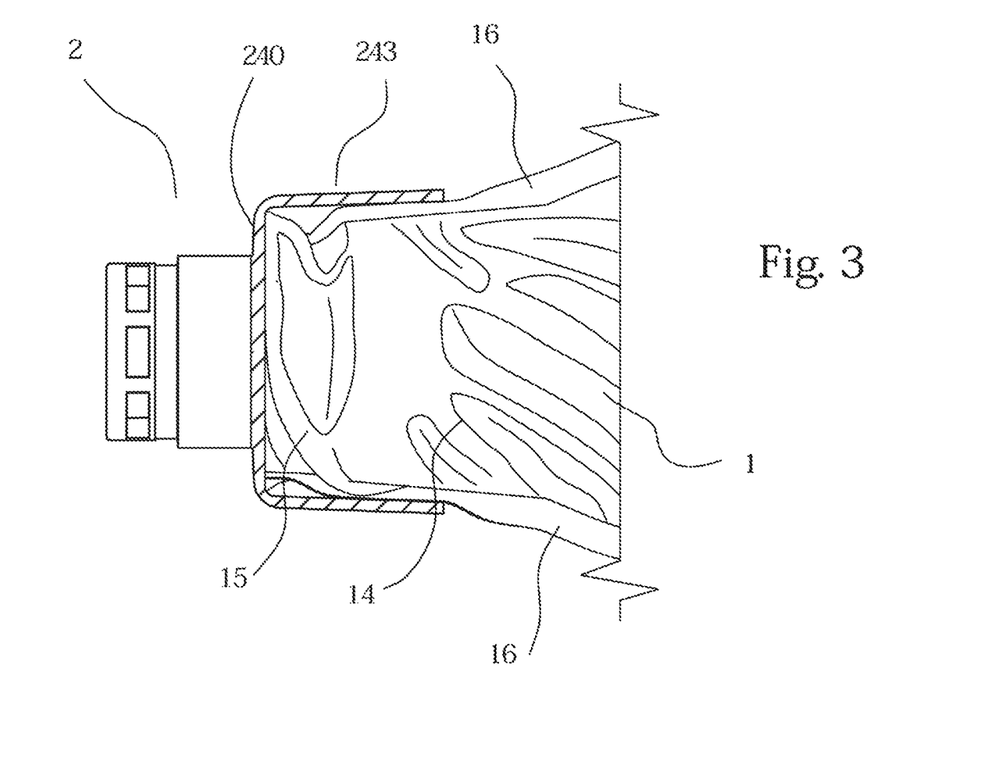
FIG. 3 depicts a side view of the coupler according to FIG. 1 connected to the driving tool, the retaining collar and the bearing collar of the coupler being depicted in section.
Figure 4:
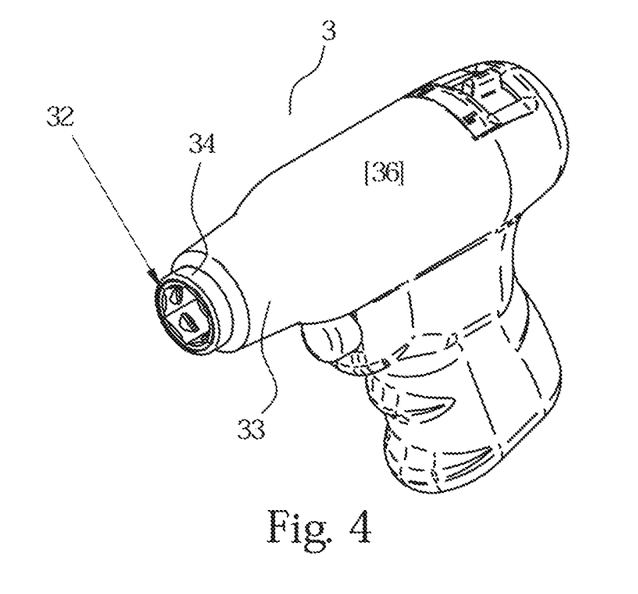
FIG. 4 depicts a perspective view of the driving tool.
Figure 5:
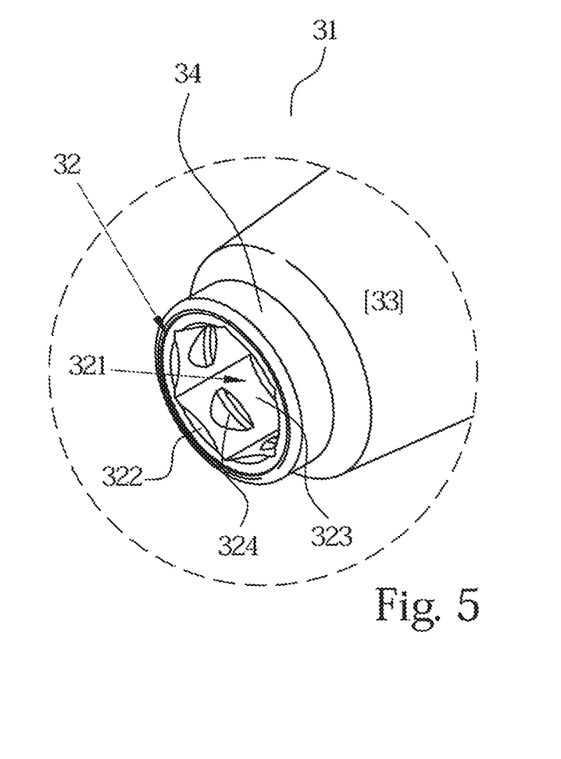
FIG. 5 depicts a detailed view of a connection end of the driving tool according to FIG. 4.
Figure 6:
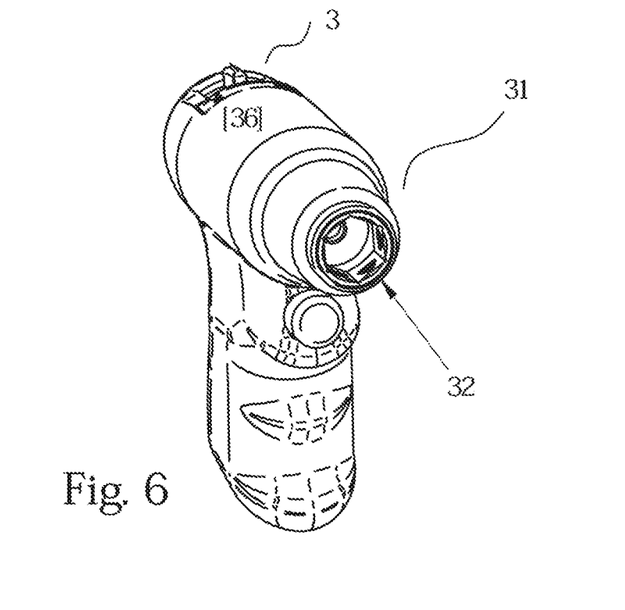
FIG. 6 depicts a perspective view of the driving tool according to FIG. 4, from a different viewing angle.
Figure 7:
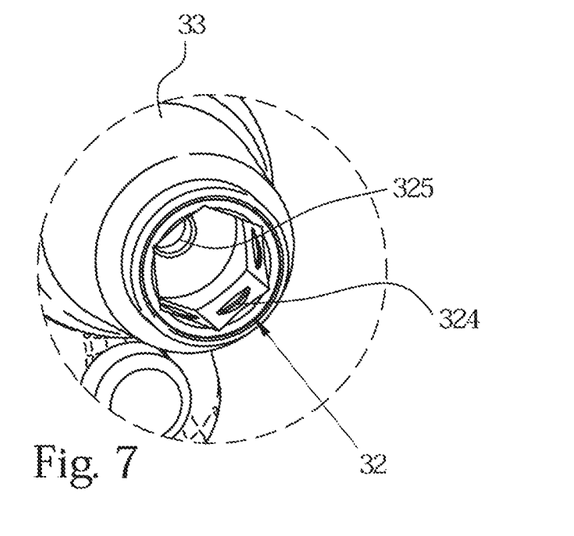
FIG. 7 depicts a detailed view of the connection end of the driving tool according to FIG. 6.

With reference to FIGS. 1 to 3, there is proposed a surgical device 10 for rotationally driving a percutaneous surgical instrument (not visible). This surgical device 10 notably comprises a driving tool 3 and a coupler 2 for coupling the driving tool 3 to a percutaneous surgical instrument. The coupler 2 allows the rotational movement generated by the driving tool to be transmitted to the percutaneous surgical instrument.

With reference to FIGS. 4 to 7, the driving tool 3 comprises a housing 36 and a rotational-drive member (not visible) arranged inside this housing 36. The housing 36 comprises a connection end 31 at which the coupler 2 can be connected to the driving tool 3.

The driving tool 3 also comprises a connection end piece 32 arranged at the connection end 31. The connection end piece 32 is configured to be connected removably to the coupler 2. The connection end piece 32 is also secured to the drive member so as to be able to transmit a rotational movement of the drive member to the coupler 2.

As a preference, the connection end piece 32 does not extend out of the housing 36, this being so as to limit the spaces in which impurities could become lodged. In other words, the connection end piece 32 preferably does not emerge from the connection end 31 of the housing 36. As a preference, the connection end piece 32 is set back from the distal end of the housing 36. This results in the connection end piece 32 being completely covered by the housing 36 when viewed from the side, as visible in FIGS. 1 and 2. This means that all the rotating parts of the driving tool 3 are covered and makes it possible to avoid any projection of particles situated on the connection end piece 32 as the latter rotates.

The drive member 3 notably comprises a motor coupled to a transmission member itself coupled to the connection end piece 32. The transmission member is preferably a reduction member able to reduce the rotational speed transmitted by the motor while at the same time increasing the torque transmitted to connection end piece 32. Alternatively, the driving tool 3 may not be provided with any reduction member so that the transmission member is able only to transmit the rotational movement of the motor to the connection end piece 32 without modifying the rotational speed or the torque. The motor is, for example, an electric motor. The drive member may therefore incorporate inside the housing 36 a battery and/or a port for connection to an electrical power supply. The battery may be rechargeable.

According to the embodiment depicted in FIGS. 4-7, the connection end piece 32 takes the form of a cavity 321 comprising a internal wall which has a rear zone 323 of hexagonal shape and a front end 322 of frustoconical shape. A chamfered groove 324 is formed in the internal wall of the cavity 321 in the region of the hexagonal rear zone 323.

In this example, the connection end piece 32 also has a blind cylindrical drilling 325 forming the end of the end piece, the axis of symmetry of which coincides with the overall axis of symmetry of the coupling end piece 32.

The surgical device 10 further comprises a sterile flexible wrapper 1 intended to at least partially cover the driving tool 3 to isolate it from the sterile environment. The flexible wrapper 1 forms a receiving cavity that receives the driving tool 3. What is meant by "flexible" is that the wrapper 1 is able to be deformed elastically under the action of a user to form an interior volume that allows the driving tool 3 to be inserted inside the wrapper 1. The flexibility of the wrapper 1 is notably defined by the thickness of the walls of which it is formed, and by its material.

The wrapper 1 is preferably formed by at least two sheets fixed together along their end edges to form the receiving cavity. These sheets are for example fixed together by welding. A return or border 16 is formed along the end edges, with a width less than or equal to 5 mm. This return 16 corresponds to a free strip formed between the end edge of the sheets and the region in which the sheets have been fixed together, for example by welding. This return 16 is notably visible in FIGS. 2, 3 and 8. This return 16 extends substantially transversely to the walls of the wrapper 1 forming the receiving cavity when an object is inserted inside this receiving cavity, notably the driving tool 3. The wrapper 1 is preferably made of a plastic material compatible with the surgical environment.

The sheets of which the wrapper 1 are formed are, for example, of a thickness less than 1 mm, preferably less than 0.5 mm, more preferably still, equal to 0.15 mm.

The flexible wrapper 1 has no rigid connection piece for connecting to the driving tool 3 or to the coupler 2. Thus, when the wrapper 1 is not mounted on the driving tool 3 or is not in the vicinity of the coupler 2, for example when the surgical device 10 is placed on a packaging tray, there is no rigid connection piece fixed to the wrapper 1. In other words, in its state disconnected or unmounted from the surgical device 10, the wrapper 1 has no rigid connection piece. This state disconnected or unmounted from the surgical device 10 corresponds to a state in which the wrapper 1, the coupler 2 and the driving tool 3 are not associated with one another, i.e. are not fixed to one another.

The coupler 2 is an individual accessory. In other words, it forms a one-piece accessory of which the subassemblies are secured and are not intended to be dissociated from one another in the use of the coupler 2. The coupler 2 may be produced as a single component or as at least two components secured to one another. It is thus possible for one of the portions of the coupler 2 to be clipped or assembled to the other portions of the coupler 2 prior to use. In all of the embodiments, the portions of the coupler 2 are not intended to be able to move relative to one another. In this way, the coupler 2 is a unit and secured-together assembly. If there is any possibility of relative movement between components, this is caused solely by assembly clearances. It is not desirable for there to be relative mobility between these portions or for particles to be able to circulate between these portions.

A first opening 13 is formed by the flexible wrapper 1. This first opening 13 is configured to allow the driving tool 3 to be inserted into the receiving cavity. The first opening 13 is dimensioned in such a way as to allow ease of insertion of the driving tool 3 into the wrapper 1. The first opening 13 is provided with two folds 17 to facilitate handling and with closure means 18 (for example adhesive) allowing the first opening 13 to be sealed closed.

The flexible wrapper 1 also forms an end portion 15 configured to receive the connection end 31 of the driving tool 3. In other words, the flexible wrapper 1 comprises a narrowing into which the tip of the driving tool 3 can be inserted. A driving tool, for example of the drill type, is usually formed of a first portion that forms a hand grip and of a second portion to which a component is coupled in order to be rotationally driven. As a preference, the tip of the driving tool 3 corresponds to this second portion so that the connection end 31 is positioned at the level of the tip of the driving tool 3.

A second opening 12 is formed at the level of the end portion and opens into the receiving cavity of the flexible wrapper 1. This second opening 12 is formed in particular at a distal end of the wrapper 1. This second opening 12 is configured to allow partial insertion of the coupler 2 into the receiving cavity through the second opening 12. As a preference, the partial insertion of the coupler 2 corresponds to the insertion of a proximal connection part of the coupler to the driving tool. Thus, the coupler 2 is connected to the driving tool through the second opening 12 of the flexible wrapper 1.

This second opening 12 is preferably formed on the opposite side of the receiving cavity from the first opening 13 so as to facilitate the positioning of the driving tool 3 in the connection end 15. Specifically, the driving tool 3 is preferably inserted into the receiving cavity with its connection end forward and then dropped inside the flexible wrapper 1 so that it positions itself under the effect of gravity and without contact by the user with the driving tool 3 so as to avoid any contamination. It is thus easier to perform this operation of positioning the driving tool 3 if the first 13 and second 12 openings are arranged opposite one another.

The flexible wrapper 1 also forms an annular sealing portion 14 arranged in the vicinity of the end portion 15, between the first 13 and second 12 openings. As a preference, the annular portion 14 is contiguous with the end portion 15.

With reference to FIGS. 1 and 2, the annular portion 14 is configured to be received in contact with the housing 36 of the driving tool 3 when the latter is engaged in the end portion 15. In particular, the annular portion 14 is configured to be brought into contact with an annular surface 33 of the housing 36 when the latter is engaged in the end portion 15.

This surface of contact between the housing 36 and the flexible wrapper 1 makes it possible to avoid the spread of impurities coming from inside the wrapper toward the second opening 12. The annular portion 14 is preferably fitted over the annular surface in such a way as to increase the area of contact and thus reduce the possibility of the spread of impurities.

The annular portion 14 of the wrapper 1 and the annular surface 33 of the housing 36 preferably have complementing shapes so as to improve still further the contact surface area. As an even greater preference, the annular portion 14 of the wrapper 1 has a cross section at least partially smaller than the cross section of the annular surface 33 of the housing 36. In this way, the annular portion 14 deforms on contact with the annular surface 33 when the driving tool is inserted into the end portion 15. This deformation allows a tight fit between the annular portion 14 and the annular surface 33, thus improving the ability of the wrapper 1 to block the passage of impurities.

Figure 8:
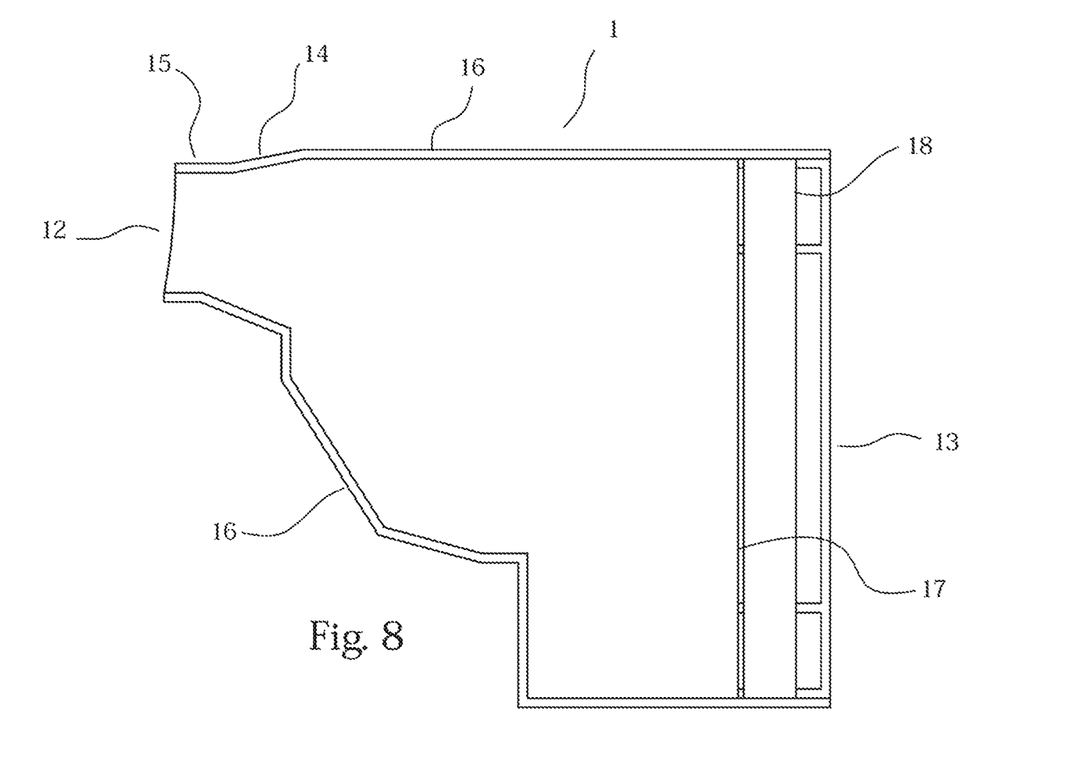
FIG. 8 depicts a side view of a sterile flexible wrapper according to FIGS. 1 to 3, into which a driving tool is to be inserted.
Figure 9:
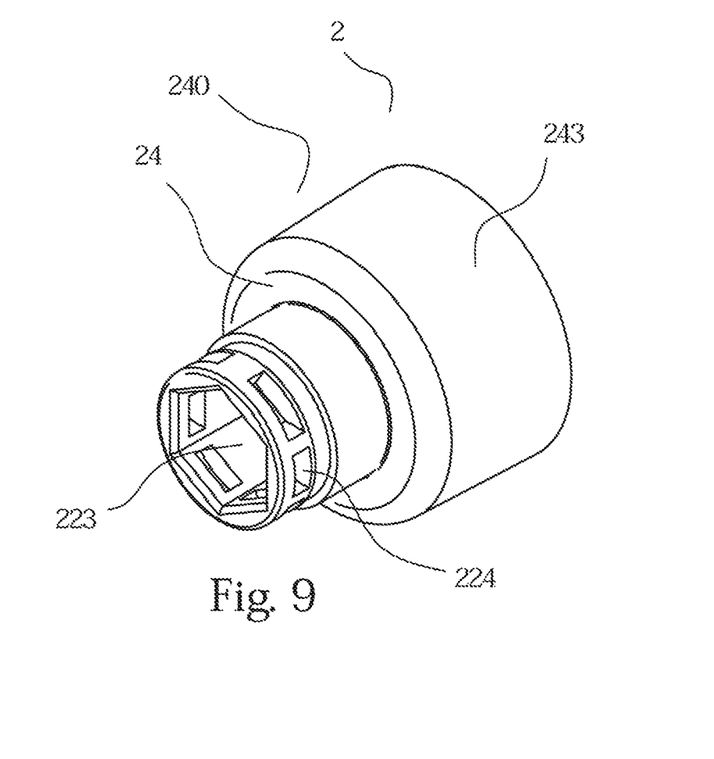
FIG. 9 depicts a perspective view of a coupler according to FIGS. 1 to 3.
Figure 10:
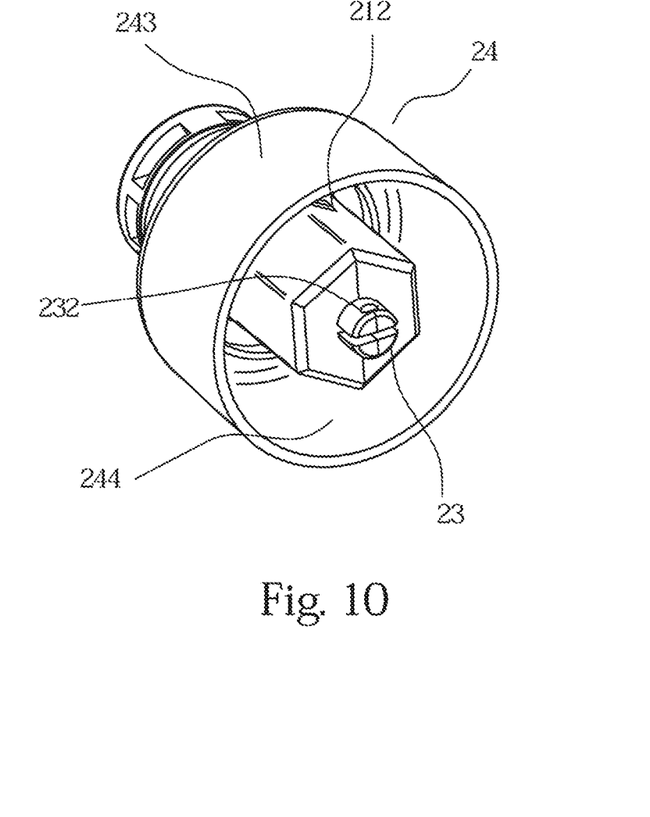
FIG. 10 depicts a perspective view of the coupler according to FIGS. 1 to 3, from a different viewing angle.
Figure 11:
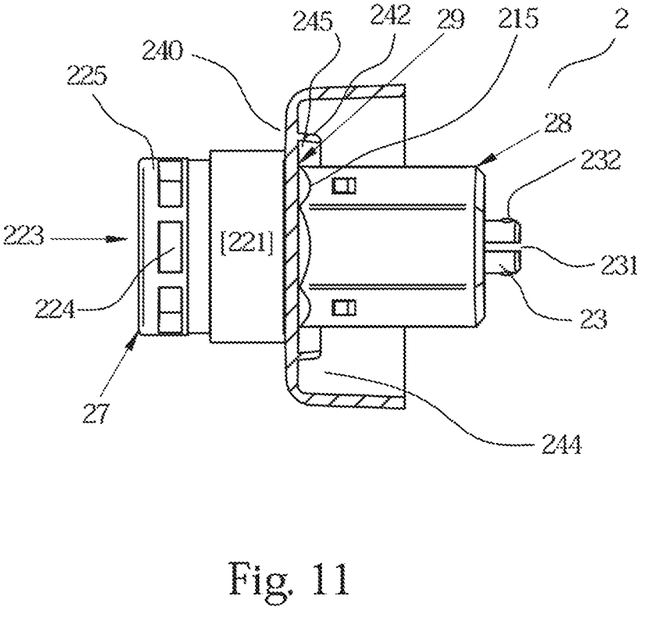
FIG. 11 depicts a perspective side view of the coupler according to FIGS. 9 and 10, the bearing and retaining collars and a protective collar of the coupler being depicted in section.

In addition, the annular portion 14 and the annular surface 33 preferably have a conically tapering cross section, as visible in FIGS. 1, 2 and 8. These conically tapering cross sections are oriented in such a way that they taper respectively toward the second opening 12 and the connection end piece 32. What is meant by "taper" is that the dimension of the cross section decreases in the direction of the second opening 12 and of the connection end piece 32, respectively.

This conical shaping allows axial and longitudinal positioning of the driving tool 3 inside the wrapper 1.

With reference to FIGS. 1 to 3 and 9 to 11, the coupler 2 has the function of allowing a percutaneous surgical instrument to be coupled to the driving tool 3 in such a way as to cause this instrument to rotate. The distal portion 27 thus forms a mechanical interface between the coupler 2 and the end of a surgical instrument.

The coupler 2 is preferably an element of elongate shape having symmetry of revolution about its longitudinal axis A.

The coupler 2 comprises a distal portion 27 configured to be connected removably to a percutaneous surgical instrument.

The distal portion 27 comprises a cylindrical body 221, of circular external cross section, defining an internal cavity forming an accommodating cavity 223 intended to receive the end of a percutaneous surgical instrument to which the driving tool 3 is to be coupled.

According to the embodiment illustrated, the distal portion 27 is intended to be placed on the outside of the wrapper 1 when the coupler 2 is connected to the driving tool 3 with the wrapper 1 positioned on the driving tool 3. The length of the distal portion 27 is chiefly defined in such a way that, when the coupler 2 is in place, a free end 225 of the distal portion 27 is situated outside of the wrapper 1.

In the embodiment considered by way of example, the accommodating cavity 223 is a cavity of hexagonal cross section on the walls of which there are formed, at the end 225, openings 224 into which fixing lugs positioned at the end of the percutaneous surgical instrument can be pushed. The end piece of the percutaneous surgical instrument may then, for example, adopt the form of a cylinder on a hexagonal base, intended to be lodged in a cylindrical cavity with hexagonal walls which is formed in a given rotation-inducing means.

The length of the end piece of the instrument, the depth of the cavity, and the general dimensions of the distal portion 27 and of the accommodating cavity 223 are chiefly defined in such a way that the assembly can be assembled with the minimum of clearance, so that use by the practitioner of said tool with a rotary end piece causes the instrument to rotate on itself about its axis of symmetry and causes the instrument to penetrate in a substantially rectilinear direction.

The couple 2 also comprises a proximal portion 28 configured to be connected removably to the driving tool 3. In particular, the proximal portion 28 is configured to be connected removably to the connection end piece 32. The proximal portion 28 thus forms a mechanical interface between the coupler 2 and the driving tool 3. The proximal portion 28 is intended to be housed at least partially inside the wrapper 1 when it is connected to the driving tool 3.

The proximal portion 28 is preferably a male connection configured to be connected to the female connection end piece 32 of the driving tool 3.

In the embodiment considered, an external wall of the proximal portion 28 forms a male element of hexagonal cross section. In that case, the connection end piece 32 is also of hexagonal cross section so that the proximal portion 28 can be inserted inside the connection end piece 32.

The proximal portion 28 may also comprise a frustoconical zone 215 configured to collaborate with a frustoconical shape 322 of the connection end piece 32. The pushing of the frustoconical zone 215 together with the frustoconical shape 322 of the connection end piece 32 allows the concentricity of the coupler 2 and of the connection end piece 32 to be maintained without clearance during use. The frustoconical zone 215 and shape 322 also have the function of creating a translational end-stop for the coupler 2 in the connection end piece 32.

The proximal portion 28 may also comprise a fixing member for fixing the coupler 2 to the connection end piece 32. With reference to FIGS. 5, 7, 10 and 11, the fixing member may comprise a cylindrical end element 23, split along its length and intended to be inserted into a blind cylindrical drilling 325 that forms the end wall of the connection end piece 32 of the driving tool 3.

The end element 23 preferably comprises a plurality of bosses 232 that form additional thicknesses such that the diameter of the cross section of the end element 23 is locally greater than the diameter of the drilling 325. The presence of a slot 231 renders the end element 23 deformable so that as the coupler 2 is coupled to the connection end piece 32 of the driving tool 3, the bosses 232 rub against the wall of the drilling 325 advantageously preventing the coupler 2 from moving freely in the connection end piece 32.

The fixing member may also comprise, at the external wall of the proximal portion 28, a plurality of chamfered bosses 212 configured to be able to become housed in a chamfered groove 324 made in an internal wall of the cavity 321 of the connection end piece 32. It thus becomes possible to block the coupler 2 in position by clipping the proximal portion 28 into the connection end piece 32.

Furthermore, the proximal portion 28 may define an internal cavity extending the cavity 223 of the distal portion 27 in such a way that the end piece of the percutaneous surgical instrument can be fully housed in the coupler 2. This cavity 223 is closed on the side of the end of the proximal portion 28.

The coupler 2 further comprises a central portion 29 arranged between the distal 27 and proximal 28 portions. The central portion 29 forms a section of the coupler 2 that is arranged between the distal 27 and proximal 28 portions. This section may be cylindrical and circular and, for example, annular.

The central portion 29 comprises a bearing collar 240 extending from the section formed by the central portion 29. The bearing collar 240 extends transversely to the coupling axis A. In other words, the bearing collar 240 extends substantially radially with respect to the coupling axis A. The bearing collar 240 forms a, preferably circular, wall extending around the section of the central portion 29.

The bearing collar 240 is configured to deform axially the distal end of the flexible wrapper 1 surrounding the driving tool 3 when the proximal portion is connected to this driving tool 3. In other words, the bearing collar 240 is configured to press against the distal end of the end portion 15 of the wrapper 1 to deform same and form an annular fold creating a seal when the coupler is mounted in the driving tool 3.

To do that, the bearing collar 240 is configured in such a way that its maximum external dimension, i.e. its outside diameter when its cross section is circular in shape, is greater than the cross section of the proximal portion 28. In other words, the bearing collar 240 thus forms a disk or a flange extending radially beyond the proximal portion 28. In particular, this maximum external dimension, or outside diameter, is equal to or greater than the maximum external dimension, or outside diameter, of the connection end 31 of the driving tool 3.

In addition, the flexible wrapper 1 is configured in such a way that a portion of the wrapper 1 that forms the second opening 12 extends beyond the connection end piece 32 when the annular portion 14 of the wrapper 1 is in contact with the annular surface 33 of the driving tool 3. This portion of the wrapper 1 is produced in such a way that its length is greater than the distance, measured along the coupling axis A, separating the distal end of the connection end piece 32 from the coupler 2. Thus, this portion of the wrapper 1 comes into contact with the bearing collar 240 and then deforms when the coupler 2 is coupled to the driving tool when the latter is inserted inside the wrapper 1. This deformed portion of the wrapper thus creates a barrier against potential impurities coming from inside the driving tool 3. Specifically, the impurities have only a very tight and tortuous pathway along which they may exit the wrapper via the second opening 12.

The effect of this deforming of the end of the wrapper 1 is notably visible in section in FIGS. 1 and 2 and in side view in FIG. 3.

In addition, when the driving tool 3 is housed inside the wrapper 1 and at the same time the coupler 2 is mounted in the connection end piece 32, the returns 16 situated at the annular portion 14 and end portion 15 deform and come into contact with the internal surface of the retaining collar 243 (see FIG. 2). This, as the coupler 2 rotates, allows retention of all the particles that may have been able to escape the seal formed by the deformation of the end of the end portion 15 against the bearing collar 240.

The central portion 29 also comprises a retaining collar 243 extending along the coupling axis A. The retaining collar 243 forms an annular wall extending along the coupling axis A. The retaining collar 243 preferably extends from one end of the bearing collar 240 so that the bearing collar 240 and retaining collar 243 are contiguous. The retaining collar 243 extends around the coupling axis A so as to form a protective bell 24 configured to cover the connection end 33 of the driving tool 3. Thus, the dimension of the retaining collar 243 along the coupling axis A is defined so that the retaining collar 243 covers this connection end 33. For that, the retaining collar 243 at least partially covers the proximal portion 28 so as to be able to keep the distal end of the flexible wrapper sterile between the retaining collar 243 and the housing 36 of the driving tool 3 when the proximal portion 28 is connected to the driving tool 3.

The retaining collar 243 preferably extends in such a way as to cover at least one third of the length of the annular portion 14 of the wrapper 1, along the coupling axis A, when the driving tool 3 is connected to the coupler 2. As a greater preference, the retaining collar 243 preferably extends in such a way as to cover substantially the length of this annular portion 14 when the driving tool 3 and the coupler 2 are in the connected state.

The retaining collar 243 is produced in such a way that its internal transverse dimension, or inside diameter when it is of circular section, is greater than the outside diameter of the connection end part 31 that it covers. Thus, the inside dimension of the retaining collar 243 allows it to be inserted around the connection end 31 of the driving tool 3.

The retaining collar 243 is preferably cylindrical. The retaining collar 243 thus forms an annular section around the proximal portion 28. An annular space 244 is thus formed between the retaining collar 243 and the proximal portion 28 to receive one end of the wrapper 1.

The retaining collar 243 and bearing collar 240 preferably have the shape of a bell or of a U-shaped cross section. The base of the U is produced by the bearing collar 240 and the arms of the U are produced by the retaining collar 243. In other words, the central portion comprises a connecting body positioned between the distal 27 and proximal 28 portions, the bearing collar 240 extending from the connecting body and forming, with the retaining collar 243, the overall shape of a U.

The coupler 2 preferably has a cylindrical or tubular overall shape with the retaining collar 243 and bearing collar 240 forming a bell or a U around this cylinder.

In addition, the end portion 15 of the wrapper 1 preferably has a maximum external dimension that is smaller than the internal dimension of the retaining collar 243 to make it easier for the wrapper 1 to be inserted into the retaining collar 243.

The retaining collar 243 comprises a distal end positioned at the level of the bearing collar 240 and a free proximal end. The retaining collar is preferably configured in such a way that the free proximal end is positioned near the housing 36 when the coupler 2 is connected to the driving tool 3. Thus, the possibilities of impurities spreading out of the annular space 244 formed by the retaining collar 243 are reduced. According to one embodiment, the retaining collar 243 and the annular surface 33 of the driving tool 3 are dimensioned so as to form a clearance less than or equal to 3 mm, preferably less than or equal to 2 mm, between the free proximal end of the retaining collar 243 and the annular surface 33 of the driving tool 3 when the driving tool 3 is connected to the coupler 2.

As visible in FIGS. 1 and 2, an annular space 244 is thus formed by the retaining collar 243 around the proximal portion 28. The distal end of the driving tool 3 is thus confined inside this annular space 244 when it is connected to the coupler 2. This allows any potential impurities coming from inside the wrapper 1 or from the driving tool 3 to be routed into this annular space 244. The annular space is closed at a first end by the bearing collar 240 and open at an opposite second end.

The central portion 29 further comprises a protective collar 242 extending along the coupling axis A between the retaining collar 243 and the proximal portion 28. In other words, the protective collar 242 extends inside the annular space 244 formed by the retaining collar 243. The protective collar 242 preferably extends from the bearing collar 240.

This protective collar 242 is configured to at least partially cover the connection end 31 of the driving tool 3 when the coupler 2 is coupled to the driving tool 3. In other words, the protective collar 242 is configured to cover a portion of the housing 36 which portion is positioned at its connection end.

This configuration of the protective collar 242 makes it possible to add an obstacle in the path of impurities coming from inside the driving tool 3. Specifically, the passage that these impurities have to follow is thus made all the more tortuous and makes it possible to reduce the risks of these impurities escaping via the annular space.

In addition, the longitudinal extension of the protective collar 242 forms an impurities-retention space 245 between the protective collar 242 and the proximal portion 28. Specifically, any potential impurities leaving the driving tool 3 are thrown into this retention space 245 under the effect of the centrifugal force generated by the rotation of the connection end piece 32.

The protective collar 242 is preferably of tapering conical cross section tapering toward the proximal portion 28. In other words, the transverse dimension of the protective collar 242 decreases from its proximal end fixed to the bearing collar 240 toward its free distal end. Thus, the retention of impurities is further improved.

According to one embodiment, the inside diameter of the protective collar 242 is greater than the outside diameter of the connection end 34 of the housing 36 so as not to generate friction when the coupler 2 is rotated.

The assembly formed by the bearing collar 240 and the retaining collar 243 may be a component added to the central portion 29 of the coupler 2 or else of one piece with this central portion 29. The protective collar 242 is preferably formed as one piece with the bearing collar 240. Thus, the protective collar 240 forms part of this assembly formed by the bearing collar 240 and the retaining collar 243.

When one or more of the collars that are the bearing collar 240, the protective collar 242 and the retaining collar 243 is an added-on collar, it is not intended to be dissociated from the proximal 28 and distal 27 portions. The coupler 2 forms a unit accessory the arrangement of which is permanent once manufactured and assembled. None of the collars that are the bearing collar 240, the protective collar 242 and the retaining collar 243 can therefore be dissociated and then temporarily or permanently assembled with some other device, for example the wrapper 1 or the driving device 3.

As a preference, the second opening 12 and the end portion 15 have a diameter smaller than the minimum inside diameter of the retaining collar 243 but greater than the maximum outside diameter of the protective collar 242. This is so as to avoid any risk of the coupler 2 being prevented from rotating by the tightening of the end portion 15 around the protective collar 242 as a result of friction between the distal end of the end portion 15 and the bearing collar 240.

As the foregoing description tends to demonstrate, the structure of the coupler 2 and of the surgical device 10 according to the invention thus advantageously, particularly in the embodiment taken by way of example, makes it possible to guarantee sealing between the receiving cavity of the wrapper 1 that is liable to enclose nonsterile equipment (the driving tool 3 in particular) and the rest of the space in which the device is used, which space is in theory sterile.

Given the technical features of the coupler 2 and of the surgical device 10 according to the invention, it is thus advantageously possible to perform removable coupling of a driving tool 3, which tool is nonsterile, to a sterile biopsy instrument in a simple way without the risk of unintentionally contaminating the sterile environment during the coupling operation or the reverse operation of separation.

It should be considered here that, given the close relationship between the structures of the respective ends of the coupler 2 and of the connection end piece 32 of the driving tool 3, which are intended to collaborate in order to connect these two elements, it is an objective of the invention to allow removable coupling of a driving tool 3, which tool is nonsterile, to a biopsy instrument which of necessity is sterile while guaranteeing the confinement of the driving tool 3, and also to ensure optimal rotation of the biopsy instrument by the driving tool 3. What is meant here by optimal is rotation that in particular makes it possible to limit the clearances there might be at the various interfaces that make up the mechanical linking connecting the driving tool 3 and the biopsy instrument.

From an operational viewpoint, the operation of sterile coupling of a biopsy instrument and of a tool for driving said instrument by means of the surgical device 10 according to the invention can be described by the following implementation steps:

- a first step in which the practitioner, fitted with sterile gloves, grasps hold of the wrapper 1 by the folds 17, opens it and offers it up to the assistant who inserts the connection end 31 of the driving tool 3 into the end portion 15 of the wrapper 1 and lets go of the driving tool 3, the latter then being retained and held by the practitioner via the wrapper 1;
- a second step during which the practitioner hermetically seals the first opening 13 of the wrapper 1 using closure means 18 arranged at said first opening 13 without touching the driving tool 3, so that the wrapper encloses the driving tool 3;
- a third step during which the practitioner assembles the connection end piece 32 of the driving tool 3 onto the proximal portion 28 of the coupler 2 until the two elements are push-fitted one into the other; the end portion 15 is thus deformed by the bearing collar 240 inside the annular space 244 formed by the retaining collar 243;
- a fourth step during which the practitioner fits the percutaneous surgical instrument by inserting it into the distal portion 27 of the coupler 2.

The invention claimed is:

1. A coupler for sterile coupling of a percutaneous surgical instrument to a rotational driving tool, extending along a coupling axis, said coupler comprising:
    a distal portion configured to be connected removably to the percutaneous surgical instrument,
    a proximal portion configured to be connected removably to the rotational driving tool,
    a central portion arranged between the distal and proximal portions, the central portion comprising:
        a connecting body arranged between the distal and proximal portions,
        a bearing collar extending from the connecting body, transversely to the coupling axis and configured to axially deform a distal end of a flexible wrapper surrounding the rotational driving tool when the proximal portion is connected to this rotational driving tool,
        a retaining collar extending along the coupling axis at least partially covering the proximal portion so as to be able to keep the distal end of the flexible wrapper between the retaining collar and a housing of the rotational driving tool when the proximal portion is connected to the rotational driving tool, the retaining collar extending from one end of the bearing collar to form an annular space around the proximal portion configured to receive the distal end of the flexible wrapper along the coupling axis,
        wherein the bearing collar forms, with the retaining collar, the overall shape of a U, and
        wherein the coupler forms a unit accessory in which the distal, proximal and central portions are secured to one another.

2. The coupler according to claim 1, wherein the distal, proximal and central portions are fixed relative to one another.

3. The coupler according to claim 1, wherein the retaining collar extends about the coupling axis in such a way as to form a protective bell configured to cover a connection end of the rotational driving tool.

4. The coupler according to claim 1, wherein the central portion further comprises a protective collar extending along the coupling axis between the retaining collar and the proximal portion.

5. The coupler according to claim 1, wherein the proximal portion is a male connection configured to connect to a female connection end piece of the rotational driving tool.

6. A sterile surgical device, comprising:
    the coupler according to claim 1,
    the flexible wrapper forming:
        a receiving cavity configured to receive the rotational driving tool,
        a first opening configured to allow the rotational driving tool to be inserted inside the receiving cavity,
        an end portion configured to receive a connection end of the driving tool, the end portion forming a second opening, opening into the receiving cavity and configured to allow partial insertion of the coupler inside the receiving cavity through the second opening,
        an annular portion,
        the retaining collar of the coupler being configured to at least partially cover the annular portion of the wrapper when the connection end of the rotational driving tool is inserted into the end portion of the wrapper with the proximal portion of the coupler connected to the connection end.

7. The surgical device according to claim 6, further comprising:
    the rotational driving tool comprising:
        a rotational drive member arranged inside the housing of the rotational driving tool, the housing of the rotational driving tool defining an annular surface for receiving the flexible wrapper at a connection end of the rotational driving tool,
        a connection end piece arranged at the connection end and configured to be connected removably to the proximal portion of the coupler, the connection end piece being secured to the rotational drive member in such a way as to transmit a rotational movement of the rotational drive member to the coupler when the proximal portion is connected to the connection end piece.

8. The surgical device according to claim 7, wherein the annular portion is configured to be received in contact with the annular surface of the housing of the rotational driving tool when the connection end of the rotational driving tool is inserted into the end portion of the wrapper.

9. The surgical device according to claim 8, wherein the annular portion of the wrapper and the annular surface of the housing of the rotational driving tool have complementing shapes.

10. The surgical device according to claim 8, wherein the annular portion of the wrapper has a cross section at least partially smaller than a cross section at the annular surface of the housing of the rotational driving tool so as to deform the wrapper when the rotational driving tool is inserted into the end portion with the annular portion and the annular surface in contact with one another.

11. The surgical device according to claim 9, wherein the annular portion and the annular surface have a conically tapering cross section respectively tapering toward the second opening and the connection end piece.

12. The surgical device according to claim 6, wherein the annular portion of the wrapper is contiguous with the end portion.

13. The surgical device according to claim 6, wherein the wrapper is formed by at least two sheets joined together at their end edges to form the receiving cavity, a return transverse to the sheets being formed along the end edges when the rotational driving tool is housed inside said wrapper.

14. The surgical device according to claim 13, wherein said at least two sheets are fixed together by welding.

15. The surgical device according to claim 6, wherein the retaining collar extends in such a way as to cover at least one third length of the annular portion along the coupling axis when the rotational driving tool is connected to the coupler.

16. The surgical device according to claim 6, with said surgical device comprising the rotational driving tool comprising:
- a rotational drive member arranged inside the housing of the rotational driving tool, the housing of the rotational driving tool defining an annular surface for receiving the flexible wrapper at a connection end of the rotational driving tool,
- a connection end piece arranged at the connection end and configured to be connected removably to the proximal portion of the coupler, the connection end piece being secured to the rotational drive member in such a way as to transmit a rotational movement of the rotational drive member to the coupler when the proximal portion is connected to the connection end piece,
- wherein the retaining collar comprises a distal end arranged at a level of the central portion of the coupler, and a free proximal end, the retaining collar and the annular surface of the rotational driving tool being dimensioned to form a clearance less than or equal to 3 mm between the proximal end of the retaining collar and the annular surface of the rotational driving tool when the rotational driving tool is connected to the coupler.

17. The surgical device according to claim 6, wherein the wrapper has no rigid component for connection to the rotational driving tool or to the coupler, when the rotational driving tool, the coupler and the wrapper are in the disconnected state.

* * * * *